United States Patent [19]

Odawara et al.

[11] Patent Number: 5,382,577

[45] Date of Patent: Jan. 17, 1995

[54] PHARMACEUTICAL COMPOSITION FOR INHIBITING PLATELET AGGREGATION

[75] Inventors: Akio Odawara, Tokyo; Yasuhiko Sasaki, Urawa; Sakae Murata, Kawagoe; Hiroshi Narita, Urawa, all of Japan

[73] Assignee: Tanabe Seiyaku Co., Ltd., Osaka, Japan

[21] Appl. No.: 14,233

[22] Filed: Feb. 5, 1993

[30] Foreign Application Priority Data

Feb. 6, 1992 [JP] Japan .................................. 4-067901

[51] Int. Cl.⁶ .................... A61K 31/55; A61K 31/44
[52] U.S. Cl. ........................................ 514/211; 514/301
[58] Field of Search .................................. 514/211, 301

[56] References Cited

U.S. PATENT DOCUMENTS

| | | | |
|---|---|---|---|
| 3,562,257 | 2/1971 | Kugita et al. | 260/239.3 |
| 4,051,141 | 9/1977 | Castaigne | 260/294.8 |
| 4,080,447 | 3/1978 | Amselem | 424/232 |
| 4,567,175 | 1/1986 | Takeda et al. | 514/211 |
| 4,590,188 | 5/1986 | Takeda et al. | 514/211 |
| 4,724,266 | 2/1988 | Satzinger et al. | 560/143 |
| 4,806,530 | 2/1989 | Langer | 514/161 |

OTHER PUBLICATIONS

Finzi, et al. (1989) Recenti Progressi in Medicina, 80(1):28-32.
Dialog Info. Svcs., File No. 72, Embase (1985-1993), Access No. 8612507 (Abstract), 1992.
The Merck Index, Tenth Edition, p. 1351, 9272, (1983).
Dialog Info. Svcs., File No. 72, Embase (1985-1993), Abstract, Access No. 7880871, Thommen, Ther. Shweiz (Germany), 1990, 6/9 (680-681).
Chemical Abstracts 101(21): 183606y, 1984.

*Primary Examiner*—Marianne M. Cintins
*Assistant Examiner*—M. Moezie
*Attorney, Agent, or Firm*—Birch, Stewart, Kolasch & Birch

[57] ABSTRACT

There is disclosed a pharmaceutical composition for inhibiting platelet aggregation comprising 5-(2-chlorobenzyl)-4,5,6,7-tetrahydrothieno[3,2-c]pyridine or a pharmaceutically acceptable salt thereof and a 1,5-benzothiazepine derivative of the formula:

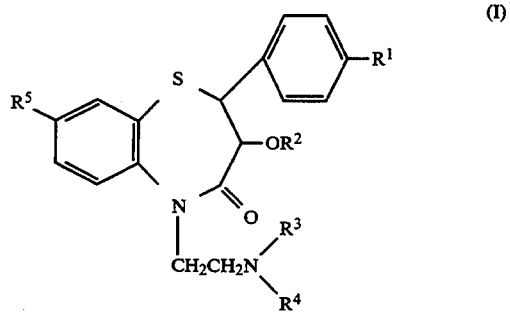

wherein $R^1$ is a lower alkyl group or a lower alkoxy group, $R^2$ is a lower alkanoyl group, $R^3$ and $R^4$ are a lower alkyl group and $R^5$ is hydrogen atom, a lower alkyl group or a halogen atom, or a pharmaceutically acceptable salt thereof.

18 Claims, No Drawings

PHARMACEUTICAL COMPOSITION FOR INHIBITING PLATELET AGGREGATION

This invention relates to a pharmaceutical composition for inhibiting platelet aggregation.

It is known that 1,5-benzothiazepine derivatives such as (+)-cis 2-(4-methoxyphenyl)-3-acetoxy-5-[2-(dimethylamino)ethyl]-2,3-dihydro-1, 5-benzothiazepin-4(5H)-one (Diltiazem) and the corresponding 8-chloro-compound (Clentiazem) have an antihypertensive, coronary vasodilating and/or platelet aggregation-inhibiting activities ( U.S. Pat. Nos. 3,562,257, 4,567,175 and 4,590,188 ). It is also known that 5-(2-chlorobenzyl)-4,5,6,7-tetrahydrothieno [3,2-c]pyridine (Ticlopidine) is useful as the platelet aggregation inhibitor[(THE MERCK INDEX, TENTH EDITION, 1351 pages, 9272( 1983 )].

As a result of the various investigations, the inventors of the present invention have now found that inhibitory effects on the platelet aggregation is enhanced in a synergistic manner by means of combined use of tidopidine and the following 1,5-benzothiazepine derivatives, compared with either agent alone. Thus, according to the present invention, there is provided a pharmaceutical composition for inhibiting platelet aggregation which comprises ticlopidine or a pharmaceutically acceptable salt thereof and a 1,5-benzothiazepine derivative of the formula:

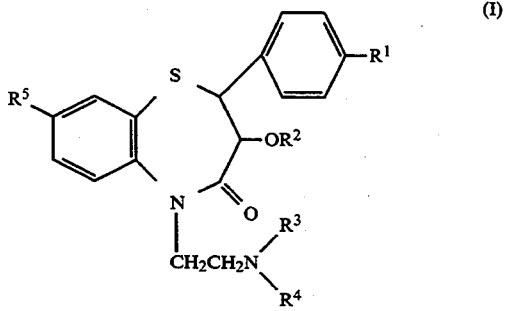

(I)

wherein $R^1$ is a lower alkyl group or a lower alkoxy group, $R^2$ is a lower alkanoyl group, $R^3$ and $R^4$ are a lower alkyl group and $R^5$ is hydrogen atom, a lower alkyl group or a halogen atom, or a pharmaceutically acceptable salt thereof.

Example of the 1,5-benzothiazepine derivatives of the present invention may include the compounds of the formula (I), wherein $R^1$ is a lower alkyl group having 1 to 4 carbon atoms or a lower alkoxy group having 1 to 4 carbon atoms, $R^2$ is a lower alkanoyl group having 2 to 5 carbon atoms, $R^3$ and $R^4$ are a lower alkyl group having 1 to 4 carbon atoms and $R^5$ is hydrogen atom, a lower alkyl group having 1 to 4 carbon atoms or a halogen atom such as chlorine, bromine and fluorine. Among them, preferred compounds (1) are those wherein $R^1$ is methyl or methoxy $R^2$ is acetyl, $R^3$ and $R^4$ are methyl, and $R^5$ is hydrogen atom, methyl or chlorine.

Since the 1,5-benzothiazepine derivatives (1) of the present invention have two asymmetric carbon atoms at 2-position and 3-position of benzothiazepine ring, there exist two kinds of stereoisomers [namely, cis- and trans-isomers] and four kinds of optical isomers [namely, (+)-cis-, (−)- cis, (+)-trans- and (−)-trans-isomers]. The present invention is inclusive either of these isomers and their mixtures. Among them, preferred isomers are (−)-cis-isomer of the compounds of the formula (I) wherein $R^1$ is a lower alkyl group, $R^2$ is a lower alkanoyl group, $R^3$, $R^4$ and $R^5$ are a lower alkyl group, and (+)-cis-isomer of the compounds of the formula (I) wherein $R^1$ is a lower alkoxy group, $R^2$ is a lower alkanoyl group, $R^3$ and $R^4$ are a lower alkyl group and $R^5$ is hydrogen atom or a halogen atom.

The ticlopidine and 1,5-benzothiazepine derivatives (I) of the present invention can be used for medical use in either the free form or in the form of pharmaceutically acceptable salt thereof. Pharmaceutically acceptable salts of ticlopidine and compound (1) include, for example, inorganic acid addition salts such as hydrochloride, hydrobromide, sulfate and phosphate, and organic acid addition salt such as oxalate, acetate, maleate, fumarate, tanrate and methanesulfonate.

A preferred weight ratio of ticlopidine or a pharmaceutically acceptable salt thereof to the 1,5-benzothiazepine derivative (I) or a pharmaceutically acceptable salt thereof is 0.1–40:1, especially 0.3–10:1.

A preferred daily dose of ticlopidine or a pharmaceutically acceptable salt thereof is 20 to 200 mg, especially 30 to 100 mg, and that of the 1,5-benzothiazepine derivatives (I) or a pharmaceutically acceptable salt thereof is 5 to 200 mg, especially 10 to 100 mg, within the range of above-mentioned ratio.

Although the composition of the present invention can be used by way of either oral administration or parenteral administration, especially oral administration is preferred. In the case of oral administration, the composition of the present invention can be used as a pharmaceutical preparation together with a pharmaceutical carrier suitable for oral administration. The pharmaceutical carriers include, for example, conventional excipients, binders, disintegrators and lubricants (e.g., starch, Eactose, glucose, gelatin, sorbitol, tragacanth gum, polyvinylpyrrolidone, sugar, corn starch, polyethylene glycol, talc, potassium phosphate and magnesium stearate). Further, the dosage form may be a solid preparation such as tablets, pills, capsules and suppositories or it may also be a liquid preparation such as solutions, suspensions and emulsions. On the other hand, in the case of parenteral administration, the composition of the present invention may be preferably used as an injection, and as the pharmaceutical carrier for this purpose, for example, distilled water for injection, vegetable oil, propylene glycol, etc., can be suitably used. If required, a dissolving agent, a buffering agent and/or a stabilizing agent may be also contained.

As described above, the pharmaceutical composition of the present invention has excellent inhibitory effects on the platelet aggregation, and therefore it can be effectively used for treatment of coronary or cerebrovascular thrombosis, peripheral vascular disease, platelet aggregation disorders and migraine.

Furthermore, the pharmaceutical composition of the present invention shows a stronger platelet aggregation-inhibiting activity as compared with single use of each component and exerts an excellent synergistic effect. Namely, the dose of each component can be reduced by means of the combined use of the components in order to obtain an effect equivalent to that obtained by single use. Therefore, the pharmaceutical preparation of the present invention is high in safety and exerts a good effect.

EXPERIMENTAL EXAMPLE
Inhibitory effect on platelet aggregation
(Method)

Nine volumes of human blood were mixed with one volume of an aqueous 3.8 % trisodium citrate solution, and the mixture was centrifuged to give platelet-rich plasma (hereinafter referred to as "PRP") as the supernatant solution. The bottom layer was further centrifuged to give platelet-poor plasma (hereinafter referred to as "PPP") as the supernatant solution. PRP was diluted with PPP so that the blood platelet counts were $4 \times 10^5/\text{mm}^3$. Then, 175 µl of said diluted PRP were added to a mixture of 25 µl of a solution of the following test compound (A), (B) or (C) and 25 µl of a solution of ticlopidine (D). After the mixture was stirred for 2 minutes at 37° C., 25 µl of a collagen solution [Horm ®, HORMON-CHEMIE] was added thereto, and the degree of platelet aggregation was measured by the method of Born [Nature, 194, page 927 (1962)].

In the control group, a mixture of 175 µl of diluted PRE 25 µl of a solution of the test compound (A), (B), (C) or (D) and 25 µl of a physiological saline solution was tested.

Further, as a non-medicated control group, a mixture of 175 µl of said diluted PRP and 50 µl of a physiological saline solution was used.

Inhibitory effect on platelet aggregation is represented by the relative proportion of platelet aggregation of test compound(s) to that of nonmedicated control. It is calculated from the following formula.

Inhibitory effect on platelet aggregation (%) =

$$\frac{\text{Platelet aggregation (\%)} - \text{Platelet aggregation (\%)}}{\text{of non-medicated control}} \times 100$$

(Test compounds)

(A) (−)-cis-2-(4-methylphenyl)-3-acetoxy-5-[2-(dimethylamino)ethyl]-8-methyl-2, 3-dihydro-1,5-benzothiazepin-4(5H)-one maleate ($R^1$, $R^3$, $R^4$ and $R^5$=methyl $R^2$=acetyl.)

(B) (+)-cis-2-(4-methoxyphenyl)-3-acetoxy-5-[2-(dimethylamino)ethyl]-8-chloro-2, 3-dihydro-1,5-benzothiazepin-4(5H)-one maleate ($R^1$=methoxy, $R^2$=acetyl, $R^3$ and $R^4$=methyl, $R^5$=chlorine.)

(C) (+)-cis-2-(4-methoxyphenyl)-3-acetoxy-5-[2-(dimethylamino)ethyl]-2,3-dihydro-1,5-benzothiazepin-4(5H)-one hydrochloride ($R^1$=methoxy, $R^2$=acetyl, $R^3$ and $R^4$=methyl, $R^5$=hydrogen atom.)

(D) Ticlopidine hydrochloride <i.e. 5-(2-chlorobenzyl)-4,5,6,7-tetrahydrothieno [3,2-c]pyridine hydrochloride>

(Result)

The results are shown in the following TABLE 1

TABLE 1

| | Concentration of test Compound (µg/ml) | | | | Inhibitory effect on platelet aggregation (%) |
|---|---|---|---|---|---|
| | (A) | (B) | (C) | (D) | |
| The present invention | 30 | — | — | 100 | 60.5 |
| | — | 30 | — | 100 | 60.5 |
| | — | — | 30 | 100 | 63.2 |
| Control | 30 | — | — | — | 21.1 |
| | — | 30 | — | — | 9.2 |

TABLE 1-continued

| | Concentration of test Compound (µg/ml) | | | | Inhibitory effect on platelet aggregation (%) |
|---|---|---|---|---|---|
| | (A) | (B) | (C) | (D) | |
| | — | — | 30 | — | 11.8 |
| | — | — | — | 100 | 5.3 |

What we claim is:

1. A pharmaceutical composition for inhibiting platelet aggregation, which comprises 5-(2-chlorobenzyl)-4,5,6,7-tetrahydrothieno pyridine or a pharmaceutically acceptable salt thereof and a 1,5-benzothiazepine derivative of the formula:

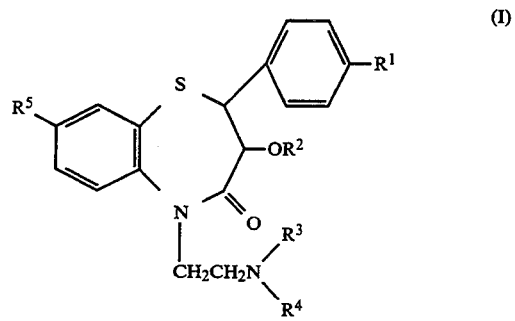

wherein $R^1$ is a lower alkyl group or a lower alkoxy group, $R^2$ is a lower alkanoyl group, $R^3$ and $R^4$ are a lower alkyl group and $R^5$ is a hydrogen atom, a lower alkyl group or a halogen atom, or a pharmaceutically acceptable salt thereof, wherein the weight ratio of 5-(2-chlorobenzyl)-4,5,6,7-tetrahydrothieno pyridine or a pharmaceutically acceptable salt thereof to the 1,5-benzothiazepine derivative (1) or a pharmaceutically acceptable salt thereof is 1–3.3:1.

2. The composition according to claim 1, wherein $R^1$ is methyl group or methoxy group, $R^2$ is acetyl group, $R^3$ and $R^4$ are methyl group and $R^5$ is hydrogen atom, methyl group or chlorine atom.

3. The composition according to claim 1, wherein $R^1$ is methyl group, $R^2$ is acetyl group, $R^3$ and $R^4$ are methyl group and $R^5$ is methyl group.

4. The composition according to claim 1, wherein $R^1$ is methoxy group, $R^2$ is acetyl group, $R^3$ and $R^4$ are methyl group and $R^5$ is hydrogen atom or chlorine atom.

5. The composition according to claim 3, wherein said 1,5-benzothiazepine derivative is a (−)-cis-isomer.

6. The composition according to claim 4, wherein said 1,5-benzothiazepine derivative is a (+)-cis-isomer.

7. The composition according to claim 1, wherein the amount of 5-(2-chlorobenzyl)-4,5,6,7-tetrahydrothieno pyridine or a pharmaceutically acceptable salt thereof is 20 to 200 mg and the amount of the 1,5-benzothiazepine derivative (1) or a pharmaceutically acceptable salt thereof is 5 to 200 mg.

8. The composition according to claim 1, wherein the amount of 5-(2-chlorobenzyl)-4,5,6,7-tetrahydrothieno pyridine or a pharmaceutically acceptable salt thereof is 10 to 100 mg and the amount of the 1,5-benzothiazepine derivative (1) or a pharmaceutically acceptable salt thereof is 10 to 30 mg.

9. A pharmaceutical composition for inhibiting platelet aggregation, which comprises 5-(2-chlorobenzyl)-4,5,6,7-tetrahydrothieno pyridine hydrochloride and (—)-cis-2-(4-methylphenyl)-3-acetoxy-5-8-methyl-2, 3-dihydro-1,5-benzothiazepin-4(5H)-one maleate, wherein the weight ratios of 5-(2-chlorobenzyl)-4,5,6,7-tetrahydrothieno pyridine hydrochloride and (—)-cis-2-(4-methylphenyl)-3-acetoxy5-8-methyl-2, 3-dihydro-1,5-benzothiazepin4(5H)-one maleate is 1–3.3:1.

10. A method for inhibiting platelet aggregation which comprises administering to a patient in need thereof a pharmaceutical composition comprising 5-(2-chlorobenzyl)-4,5,6,7-tetrahydrothieno pyridine or a pharmaceutically acceptable salt thereof and a 1,5-benzothiazepine derivative of the formula:

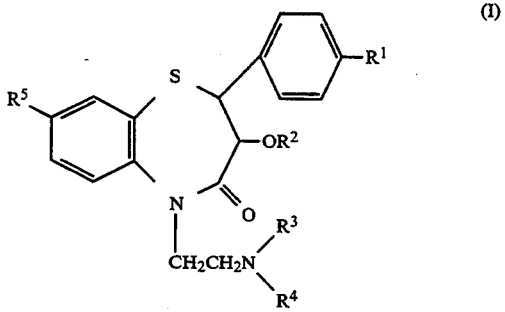

(I)

wherein $R^1$ is a lower alkyl group or a lower alkoxy group, $R^2$ is a lower alkanoyl group, $R^3$ and $R^4$ are a lower alkyl group and $R^5$ is hydrogen atom, a lower alkyl group or a halogen atom, or a pharmaceutically acceptable salt thereof in a combined amount effective for inhibiting platelet aggregation, wherein the weight or a pharmaceutically acceptable salt thereof to the 1,5-benzothiazepine derivative (1) or a pharmaceutically acceptable salt thereof is 0.1–3.3:1.

11. The method according to claim 10, wherein $R^1$ is methyl group or methoxy group, $R^2$ is acetyl group, $R^3$ and $R^4$ are methyl group and $R^5$ is hydrogen atom, methyl group or chlorine atom.

12. The method according to claim 10, wherein $R^1$ is methyl group, $R^2$ is acetyl group, $R^3$ and $R^4$ are methyl group and $R^5$ is methyl group.

13. The method according to claim 10, wherein $R^1$ is methoxy group, $R^2$ is acetyl group, $R^3$ and $R^4$ are methyl group and $R^5$ is hydrogen atom or chlorine atom.

14. The method according to claim 12, wherein said 1,5-benzothiazepine derivative is a (—)-cis-isomer.

15. The method according to claim 13, wherein said 1,5-benzothiazepine derivative is a (+)-cis-isomer.

16. The method according to claim 10, wherein the amount of 5-(2-chlorobenzyl)-4,5,6,7-tetrahydrothieno pyridine or a pharmaceutically acceptable salt thereof is 20 to 200 mg and the amount of the 1,5-benzothiazepine derivative (1) or a pharmaceutically acceptable salt thereof is 5 to 200 mg.

17. The method according to claim 10, wherein the amount of 5-(2-chlorobenzyl)-4,5,6,7-tetrahydrothieno pyridine or a pharmaceutically acceptable salt thereof is 10 to 100 mg and the amount of the 1,5-benzothiazepine derivative (1) or a pharmaceutically acceptable salt thereof is 10 to 30 mg.

18. A method for inhibiting platelet aggregation, which comprises administering to a patient in need thereof a pharmaceutical composition comprising 5-(2-chlorobenzyl)-4,5,6,7-tetrahydrothieno pyridine hydrochloride and (—)-cis-2-(4-methylphenyl)-3-acetoxy-5-8-methyl-2, 3-dihydro-1,5-benzothiazepin-4(5H)-one maleate, wherein the weight ratios of 5-(2-chlorobenzyl)-4,5,6,7-tetrahydrothieno pyridine hydrochloride and (—)-cis-2-(4-methylphenyl)-3-acetoxy5-8-methyl-2,3-dihydro-1,5-benzothiazepin-(4(5H)-one maleate is 1–3.3:1.

* * * * *